(12) United States Patent
MacNeille et al.

(10) Patent No.: US 9,688,194 B2
(45) Date of Patent: Jun. 27, 2017

(54) IN-VEHICLE PARTICULATE SENSOR DATA ANALYSIS

(71) Applicant: Ford Global Technologies, LLC, Dearborn, MI (US)

(72) Inventors: Perry Robinson MacNeille, Lathrup Village, MI (US); Oleg Yurievitch Gusikhin, West Bloomfield, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 125 days.

(21) Appl. No.: 14/670,129

(22) Filed: Mar. 26, 2015

(65) Prior Publication Data

US 2016/0280160 A1    Sep. 29, 2016

(51) Int. Cl.
| | | |
|---|---|---|
| *B60R 16/037* | (2006.01) |
| *B60Q 9/00* | (2006.01) |
| *G05B 15/02* | (2006.01) |
| *G01C 21/34* | (2006.01) |
| *G07C 5/00* | (2006.01) |

(Continued)

(52) U.S. Cl.
CPC .............. *B60Q 9/00* (2013.01); *B60H 1/008* (2013.01); *B60H 1/00771* (2013.01); *G01C 21/3461* (2013.01); *G05B 15/02* (2013.01); *G07C 5/008* (2013.01); *G01N 15/06* (2013.01)

(58) Field of Classification Search
CPC ...... B60Q 9/00; G05B 15/02; G01C 21/3461; G07C 5/008; G01N 15/06; B60H 1/00771; B60H 1/008
See application file for complete search history.

(56) References Cited

U.S. PATENT DOCUMENTS

| | | | | |
|---|---|---|---|---|
| 5,436,541 A | * | 7/1995 | Mangler | ............... B60S 1/0818 318/443 |
| 5,780,719 A | * | 7/1998 | VanDam | ............... B60S 1/0818 318/483 |
| 6,206,775 B1 | | 3/2001 | Lemaitre et al. | |

(Continued)

OTHER PUBLICATIONS

Szwabowski, Steven J., et al., In-Vehicle Ambient Condition Sensing Based on Wireless Internet Access, Paper No. 2010-01-0461, SAE International, Apr. 12, 2010, 1 page.

(Continued)

*Primary Examiner* — Richard Camby
(74) *Attorney, Agent, or Firm* — Franklin A. MacKenzie; Brooks Kushman P.C.

(57) ABSTRACT

A vehicle may include particulate sensors configured to generate particulate data indicative of size and quantity of ambient particulates. The vehicle may also include a computing device configured to receive the particulate data from the at least one particulate sensor, compare the particulate data to a signature data identifying a particulate condition, and adjust a vehicle setting to address the particulate condition or alert the user of the particulate condition. A server may receive a route request from a vehicle over a communications network, the route request specifying a destination location for a vehicle and an indication of signature data descriptive of particulate to avoid; construct a route avoiding the particulate according to particulate data received from a plurality of vehicles and including location metadata and time metadata; and send the route to the vehicle responsive to the request.

9 Claims, 5 Drawing Sheets

(51) Int. Cl.
    *B60H 1/00*        (2006.01)
    *G01N 15/06*      (2006.01)

(56) References Cited

U.S. PATENT DOCUMENTS

| | | | |
|---|---|---|---|
| 6,313,454 B1 * | 11/2001 | Bos | B60N 2/002 |
| | | | 250/208.1 |
| 7,857,892 B2 | 12/2010 | Marra | |
| 8,092,285 B2 | 1/2012 | Mathur et al. | |
| 8,126,620 B2 * | 2/2012 | Ringwald | A01B 69/008 |
| | | | 141/192 |
| 8,907,803 B2 | 12/2014 | Martin | |
| 8,910,298 B2 | 12/2014 | Gettings et al. | |
| 2009/0323046 A1 * | 12/2009 | Tan | E01H 1/00 |
| | | | 356/4.01 |
| 2013/0144527 A1 | 6/2013 | Kuhnreichi | |

OTHER PUBLICATIONS

Hering, Susanne, V., Ph.D., Impactors, Cyclones, and Other Inertial and Gravitational Collectors, Chapter 14, available at http://www.industrialventilation.net/ClassDownloads/IHS_725/L11%20Impactor%20Data%20Reduction/impactorscyclonesch14p1.pdf, last accessed Mar. 26, 2015, 11 pages.

Mehdizadeh, E., et al., Aerosol Impactor With Embedded MEMS Resonant Mass Balance for Real-Time Particulate Mass Concentration Monitoring, Transducers 2013, Barcelona, Spain Jun. 16-20, 2013, 4 pages.

Page, Steven J., et al., Thermally Induced Filter Bias in TEOM Mass Measurement, available at http://www.cdc.gov/niosh/mining/UserFiles/works/pdfs/tifbi.pdf, last accessed Mar. 26, 2015, 8 pages.

\* cited by examiner

IN-VEHICLE PARTICULATE SENSOR DATA ANALYSIS

TECHNICAL FIELD

Aspects of the disclosure relate to data analysis of particulate data identified by in-vehicle particulate sensors.

BACKGROUND

Particulate sensors are capable of detecting concentration distribution of particles in air over predetermined timeframes. The concentration distribution may include, for example, information on identified particles by number and/or by mass. In many cases, particulates are something to be avoided, if possible, for reasons of human health, human comfort, environmental quality and visibility, and negative effect on electrical or mechanical devices.

SUMMARY

In a first illustrative embodiment, a vehicle includes at least one particulate sensor configured to generate particulate data indicative of size and quantity of ambient particulates; and a computing device configured to receive the particulate data from the at least one particulate sensor, compare the particulate data to a particulate signature identifying a particulate condition, and adjust at least one setting of the vehicle to address the particulate condition.

In a second illustrative embodiment, a server is configured to receive a route request from a vehicle over a communications network, the route request specifying a destination location for a vehicle and an indication of signature data descriptive of particulate to avoid; construct a route avoiding the particulate according to particulate data received from a plurality of vehicles and including location metadata and time metadata; and send the route to the vehicle responsive to the request.

In a third illustrative embodiment, a computer-implemented method includes receiving first particulate data from a first vehicle particulate sensor and second particulate data from a second vehicle particulate sensor; comparing the first and second particulate data to signature data identifying a particulate condition; and when only one of the first and second particulate data matches the signature data, one of (i) adjusting a vehicle setting to address the particulate condition and (ii) alerting the user of the particulate condition.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

A vehicle may be equipped with particulate sensors located in various places in or on the vehicle. As some examples, particulate sensors may be placed in locations to monitor exhaust air quality, ambient air quality above the vehicle, ambient air quality below the vehicle, cabin air quality, air quality at engine air intake of the vehicle, air in tire well areas to monitor brake and tire wear particles, and air in near a gas tank or filling location to monitor fuel tank vapors. The vehicle may be configured to receive data from the particulate sensors indicative of the detect quantities and sizes of particulates. The vehicle may be further connected to the Internet cloud through a variety of mechanisms. Through use of the particulate sensors and cloud connectivity, new vehicle functionalities may be achieved.

Figure 1A:
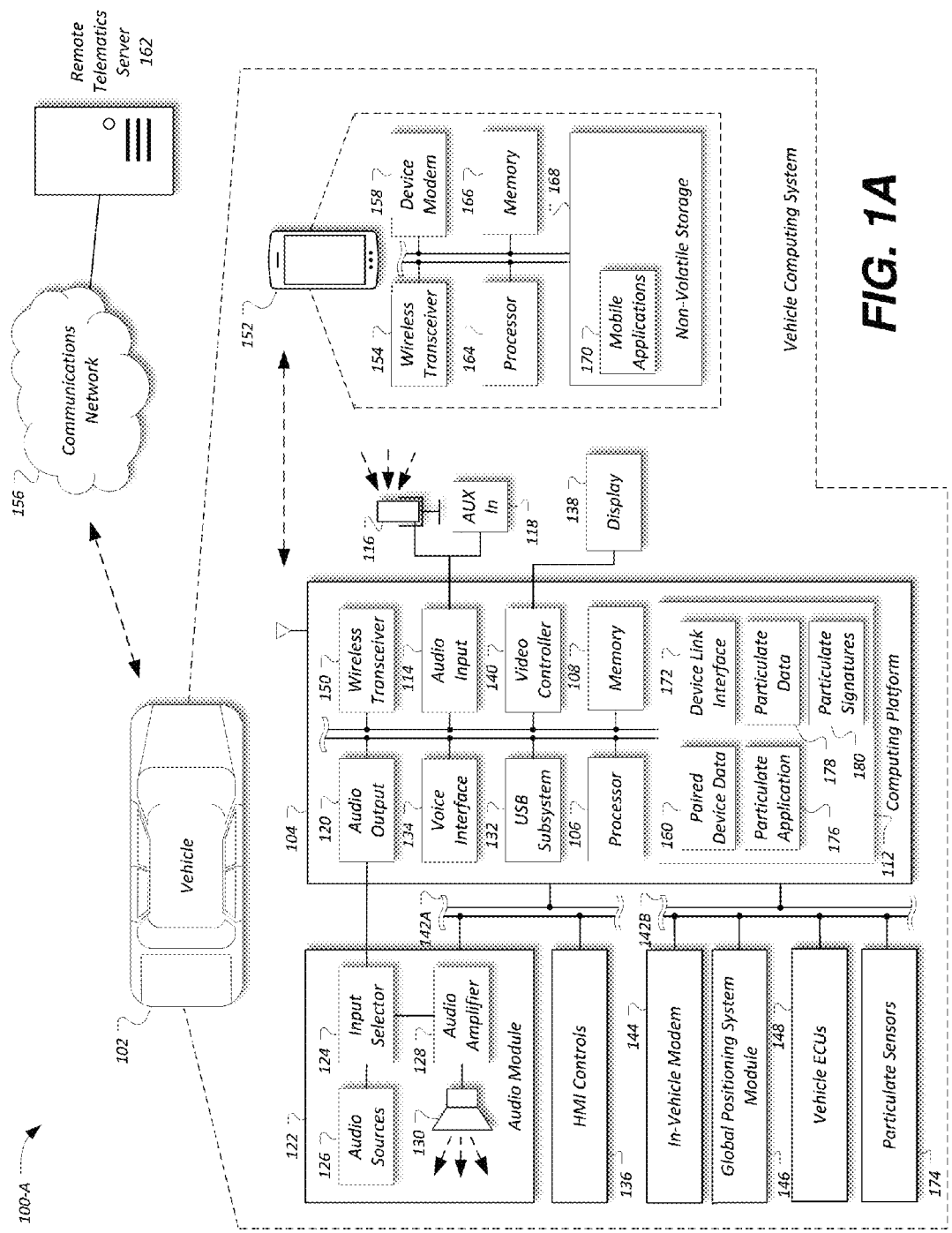
FIG. 1A illustrates an example diagram of a system that may be used to provide telematics services to a vehicle.

FIG. 1 illustrates an example diagram of a system 100-A that may be used to provide telematics services to a vehicle 102. The vehicle 102 may be one of various types of passenger vehicles, such as a crossover utility vehicle (CUV), a sport utility vehicle (SUV), a truck, a recreational vehicle (RV), a boat, a plane or other mobile machine for transporting people or goods. Telematics services may include, as some non-limiting possibilities, navigation, turn-by-turn directions, vehicle health reports, local business search, accident reporting, and hands-free calling. In an example, the system 100-A may include the SYNC system manufactured by The Ford Motor Company of Dearborn, Mich. It should be noted that the illustrated system 100-A is merely an example, and more, fewer, and/or differently located elements may be used.

The computing platform 104 may include one or more processors 106 configured to perform instructions, commands and other routines in support of the processes described herein. For instance, the computing platform 104 may be configured to execute instructions of vehicle applications 110 to provide features such as navigation, accident reporting, satellite radio decoding, and hands-free calling. Such instructions and other data may be maintained in a non-volatile manner using a variety of types of computer-readable storage medium 112. The computer-readable medium 112 (also referred to as a processor-readable medium or storage) includes any non-transitory medium (e.g., a tangible medium) that participates in providing instructions or other data that may be read by the processor 106 of the computing platform 104. Computer-executable instructions may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL.

The computing platform 104 may be provided with various features allowing the vehicle occupants to interface with the computing platform 104. For example, the computing platform 104 may include an audio input 114 configured to receive spoken commands from vehicle occupants through a connected microphone 116, and auxiliary audio input 118 configured to receive audio signals from connected devices. The auxiliary audio input 118 may be a physical connection, such as an electrical wire or a fiber optic cable, or a wireless input, such as a BLUETOOTH audio connection. In some examples, the audio input 114 may be configured to provide audio processing capabilities, such as pre-amplification of low-level signals, and conversion of analog inputs into digital data for processing by the processor 106.

The computing platform 104 may also provide one or more audio outputs 120 to an input of an audio module 122 having audio playback functionality. In other examples, the computing platform 104 may provide the audio output to an occupant through use of one or more dedicated speakers (not illustrated). The audio module 122 may include an input selector 124 configured to provide audio content from a selected audio source 126 to an audio amplifier 128 for playback through vehicle speakers 130 or headphones (not illustrated). The audio sources 126 may include, as some examples, decoded amplitude modulated (AM) or frequency modulated (FM) radio signals, and audio signals from compact disc (CD) or digital versatile disk (DVD) audio playback. The audio sources 126 may also include audio received from the computing platform 104, such as audio content generated by the computing platform 104, audio content decoded from flash memory drives connected to a universal serial bus (USB) subsystem 132 of the computing platform 104, and audio content passed through the computing platform 104 from the auxiliary audio input 118.

The computing platform 104 may utilize a voice interface 134 to provide a hands-free interface to the computing platform 104. The voice interface 134 may support speech recognition from audio received via the microphone 116 according to grammar associated with available commands, and voice prompt generation for output via the audio module 122. In some cases, the system may be configured to temporarily mute or otherwise override the audio source specified by the input selector 124 when an audio prompt is ready for presentation by the computing platform 104 and another audio source 126 is selected for playback.

The computing platform 104 may also receive input from human-machine interface (HMI) controls 136 configured to provide for occupant interaction with the vehicle 102. For instance, the computing platform 104 may interface with one or more buttons or other HMI controls configured to invoke functions on the computing platform 104 (e.g., steering wheel audio buttons, a push-to-talk button, instrument panel controls, etc.). The computing platform 104 may also drive or otherwise communicate with one or more displays 138 configured to provide visual output to vehicle occupants by way of a video controller 140. In some cases, the display 138 may be a touch screen further configured to receive user touch input via the video controller 140, while in other cases the display 138 may be a display only, without touch input capabilities.

The computing platform 104 may be further configured to communicate with other components of the vehicle 102 via one or more in-vehicle networks 142. The in-vehicle networks 142 may include one or more of a vehicle controller area network (CAN), an Ethernet network, and a media oriented system transfer (MOST), as some examples. The in-vehicle networks 142 may allow the computing platform 104 to communicate with other vehicle 102 systems, such as a vehicle modem 144 (which may not be present in some configurations), a global positioning system (GPS) module 146 configured to provide current vehicle 102 location and heading information, and various vehicle ECUs 148 configured to cooperate with the computing platform 104. As some non-limiting possibilities, the vehicle ECUs 148 may include a powertrain control module configured to provide control of engine operating components (e.g., idle control components, fuel delivery components, emissions control components, etc.) and monitoring of engine operating components (e.g., status of engine diagnostic codes); a body control module configured to manage various power control functions such as exterior lighting, interior lighting, keyless entry, remote start, and point of access status verification (e.g., closure status of the hood, doors and/or trunk of the vehicle 102); a radio transceiver module configured to communicate with key fobs or other local vehicle 102 devices; and a climate control management module configured to provide control and monitoring of heating and cooling system components (e.g., compressor clutch and blower fan control, temperature sensor information, etc.).

As shown, the audio module 122 and the HMI controls 136 may communicate with the computing platform 104 over a first in-vehicle network 142-A, and the vehicle modem 144, GPS module 146, and vehicle ECUs 148 may communicate with the computing platform 104 over a second in-vehicle network 142-B. In other examples, the computing platform 104 may be connected to more or fewer in-vehicle networks 142. Additionally or alternately, one or more HMI controls 136 or other components may be connected to the computing platform 104 via different in-vehicle networks 142 than shown, or directly without connection to an in-vehicle network 142.

The computing platform 104 may also be configured to communicate with mobile devices 152 of the vehicle occupants. The mobile devices 152 may be any of various types of portable computing device, such as cellular phones, tablet computers, smart watches, laptop computers, portable music players, or other devices capable of communication with the computing platform 104. In many examples, the computing platform 104 may include a wireless transceiver 150 (e.g., a BLUETOOTH module, a ZIGBEE transceiver, a Wi-Fi transceiver, an IrDA transceiver, an RFID transceiver, etc.) configured to communicate with a compatible wireless transceiver 154 of the mobile device 152. Additionally or alternately, the computing platform 104 may communicate with the mobile device 152 over a wired connection, such as via a USB connection between the mobile device 152 and the USB subsystem 132.

The communications network 156 may provide communications services, such as packet-switched network services (e.g., Internet access, VoIP communication services), to devices connected to the communications network 156. An example of a communications network 156 may include a cellular telephone network. Mobile devices 152 may provide network connectivity to the communications network 156 via a device modem 158 of the mobile device 152. To facilitate the communications over the communications network 156, mobile devices 152 may be associated with unique device identifiers (e.g., mobile device numbers (MDNs), Internet protocol (IP) addresses, IEEE 802.11 media access control (MAC) identifiers, etc.) to identify the communications of the mobile devices 152 over the communications network 156. In some cases, occupants of the vehicle 102 or devices having permission to connect to the computing platform 104 may be identified by the computing platform 104 according to paired device data 160 maintained in the storage medium 112. The paired device data 160 may indicate, for example, the unique device identifiers of mobile devices 152 previously paired with the computing platform 104 of the vehicle 102, such that the computing platform 104 may automatically reconnected to the mobile devices 152 referenced in the paired device data 160 without user intervention.

When a mobile device 152 that supports network connectivity is connected (e.g., paired for 802.15 Bluetooth, joined for 802.11, setup for USB) with the computing platform 104, the mobile device 152 may allow the computing platform 104 to use the network connectivity of the device modem 158 to communicate over the communications network 156 with the remote telematics server 162. In one example, the computing platform 104 may utilize a data-over-voice plan or data plan of the mobile device 152 to communicate information between the computing platform 104 and the communications network 156. Additionally or alternately, the computing platform 104 may utilize the vehicle modem 144 to communicate information between the computing platform 104 and the communications network 156, without use of the communications facilities of the mobile device 152.

Similar to the computing platform 104, the mobile device 152 may include one or more processors 164 configured to execute instructions of mobile applications 170 loaded to a memory 166 of the mobile device 152 from storage medium 168 of the mobile device 152. In some examples, the mobile applications 170 may be configured to communicate with the computing platform 104 via the wireless transceiver 154 and with the remote telematics server 162 or other network services via the device modem 158. The computing platform 104 may also include a device link interface 172 to facilitate the integration of functionality of the mobile applications 170 into the grammar of commands available via the voice interface 134 as well as into display 138 of the computing platform 104. The device link interfaced 172 may also provide the mobile applications 170 with access to vehicle information available to the computing platform 104 via the in-vehicle networks 142. Some examples of device link interfaces 172 include the SYNC APPLINK component of the SYNC system provided by The Ford Motor Company of Dearborn, Mich., the CarPlay protocol provided by Apple Inc. of Cupertino, Calif., or the Android Auto protocol provided by Google, Inc. of Mountain View, Calif.

The particulate sensors 174 include devices configured to detect a concentration distribution (by number and/or mass) of particles in air over a time frame (e.g., one second, etc.). In an example, the particulate sensors 174 may include micro-electromechanical systems (MEMS) sensor designs based on impactor sensor designs, having progressively finer filters for particulates. For instance, the particulate sensors 174 may be configured to sample or measure particles having an aerodynamic diameter greater than a mean free path of air (~70 nm) and that behave as aerosols in that they are primarily transported through the air in suspension (>1 μm) or as a colloidal system (<1 μm). Aerodynamic diameter may refer to a measure of particulate size, and may be indicated as a measure of a diameter of a water droplet that has the same sedimentation rate as the particle being measured. The particles being measured, for instance, may be composed of biological materials, dust, inorganic and non-biologic organic materials, and gas molecules as some possibilities. Examples of measurable particulates may accordingly include haze, dust, particulate air pollutants and smoke. The measured data from the particulate sensors 174 indicative of size and quantity of detected particles may be referred to herein as particulate data 178.

As the particulate sensors 174 may include a sequence of sensors configured to detect a distribution of particles according to their particle sizes, these particulate data 178 distributions of detected particle quantities and sizes may be used as a fingerprint or particulate signature 180 for sources of particle emission. In a more specific example, the particulate signature 180 may include one or more ranges of particulate quantities for particulates within one or more specified particulate size ranges. In some cases, the particulate size ranges may correspond to the detection ranges for the progressively finer filters of the particulate sensors 174. In some cases, the particulate ranges may include only at least a minimum quantity or only at most a maximum quantity, while in other cases the ranges may include both a minimum and a maximum quantity. In some cases, the quantities may also be relative to the quantities of other detected particles, e.g., that a particulate signature 180 may match upon at least a minimum quantity of particles being detected in a first range of particle sizes, and detection of twice as many particulates in a second range as detected in the first range.

In an example of use of the particulate signatures 180, softwood particulates may have measurably lower concentration of particulates in the range of 0.3-0.6 μM than do hardwood particulates from a wood burning stove. Thus, particulate signatures 180 may be defined using these differences in particulates and used to distinguish particulate data 178 indicative of softwood from particulate data 178 indicative of hardwood, as one example. Similarly, particulate signatures 180 may be defined to detect various other conditions, such as smog, ice, fog, tire wear, brake wear, as some other possibilities.

The particulate application 176 may be configured to receive the particulate data 178 from the particulate sensors 174, identify the particulate indicated by the particulate data 178 based on the particulate signatures 180, and make determinations on vehicle 102 actions to be performed based on the identified particulate. In some cases, the determinations may be made based on local vehicle 102 information, while in other cases, the determinations may be made at least in part based on information received from the remote telematics server 162, such as particulate data 178 sourced from other vehicles 102 or particulate signatures 180 of particulate emitters retrieved from the remote telematics server 162. The particulate application 176 may also be configured to provide particulate data 178 sourced from the particulate sensors 174 of the vehicle 102 to the remote telematics server 162 to aid in decision-making by other vehicles 102, as well as to provide for analysis of crowd-sourced particulate data 178 and vehicle routing around particle emissions.

Figure 1B:
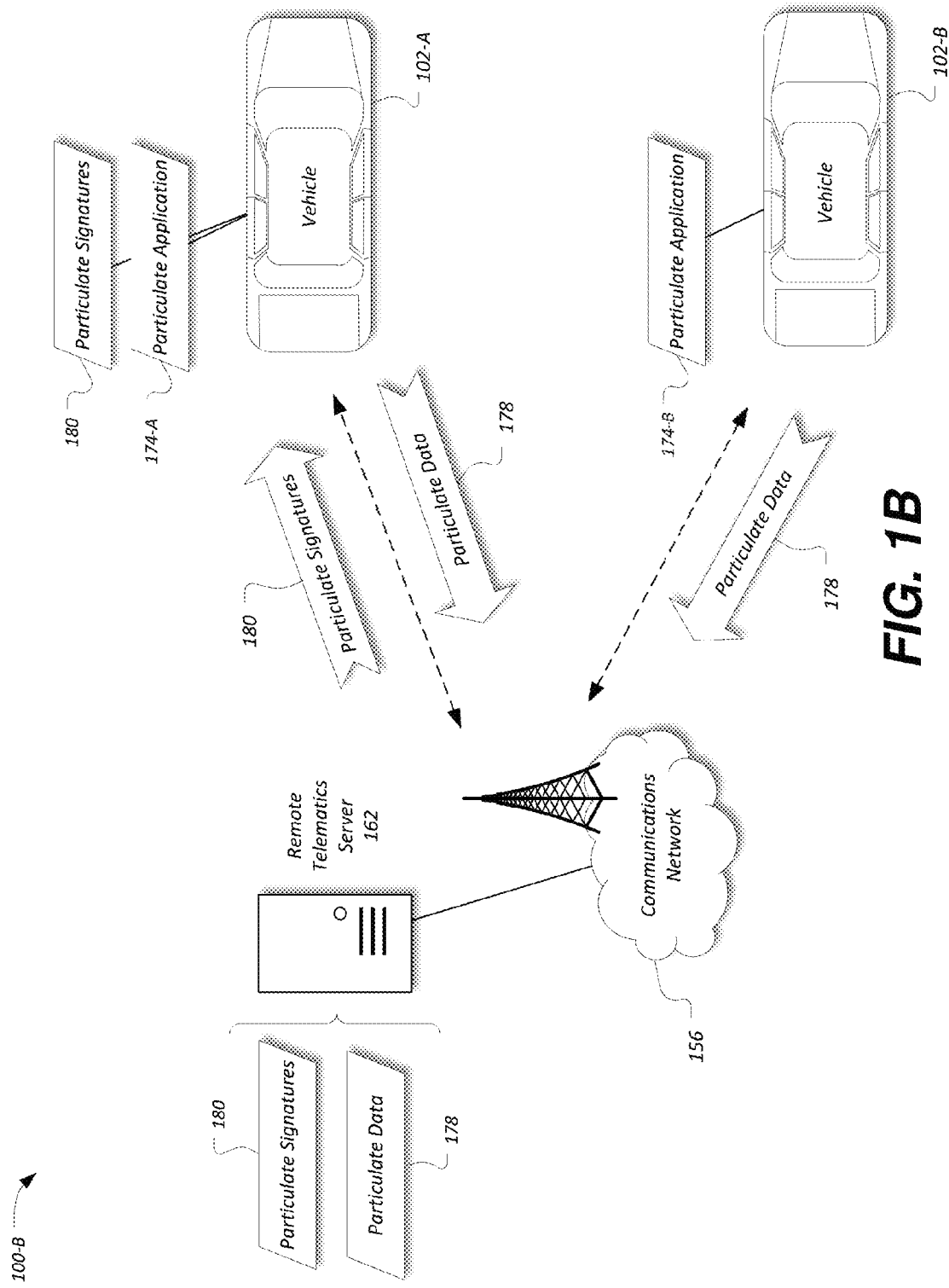
FIG. 1B illustrates an example portion of the system configured to aggregate particulate data from the particulate sensors via the remote telematics server.

FIG. 1B illustrates an example portion of the system 100-B configured to aggregate particulate data 178 from the particulate sensors 174 via the remote telematics server 162. As shown, the remote telematics server 162 may be configured to maintain particulate data 178 information received from vehicle 102-A and 102-B (collectively vehicles 102). In turn, the vehicles 102 may be configured to access the remote telematics server 162 to retrieve particulate data 178 relevant to the current vehicle location, and utilize the information to make determinations regarding vehicle 102 actions to be performed. In some cases, the vehicle 102 may be configured to communicate with the remote telematics server 162 using the data services of the connected mobile device 152. The vehicle 102 may additionally or alternately be configured to communicate with the remote telematics server 162 using the in-vehicle modem 144 of the vehicle 102, if so equipped. While two vehicles 102-A and 102-B are shown, it should be noted that systems may have many more vehicles 102. As another possibility, in some cases the system 100-B may include multiple remote telematics servers 162, for purposes such as redundancy and/or for different servers to operate in different regions.

The particulate application 176 may be configured to retrieve particulate data 178 from the particulate sensors 174. The particulate data 178 may include information indicative of the size and quantity of particulate detected by the vehicle particulate sensors 174. In some cases, the particulate application 176 may simply compile the particulate data 178 received from the vehicle particulate sensors 174, while in other cases the particulate application 176 may perform analysis on the particulate data 178, such as to compare a distribution of particle sizes of the particulate data 178 to predefined particulate signatures 180 that may be used to identify the type of emission. If identification is performed, in some cases the particulate application 176 may additionally or alternately include the analyzed data in the particulate data 178.

The particulate application 176 may also determine a current location of the vehicle 102, such as by accessing the GPS module 146, to retrieve current location coordinates of the vehicle 102. Using the current location and particulate data 178, the particulate application 176 may be configured to send information to the remote telematics server 162 indicative of particulate conditions at the vehicle 102. This information may include, for example, the particulate data 178 as collected and/or an indication of a match to particular particulate signature 180.

The particulate application 176 may also be configured to receive particulate data 178 from the remote telematics server 162 sourced from other vehicles 102. In an example, the particulate application 176 may determine the current location of the vehicle 102, such as by accessing the GPS module 146, to retrieve current location coordinates of the vehicle 102. Using the current location, the particulate application 176 may query the remote telematics server 162 for particulate data 178 for the determined location of the vehicle 102. Accordingly, the particulate application 176 may be configured to utilize particulate data sourced from other vehicles 102 to aid in decision-making by the vehicles 102.

Figure 2:
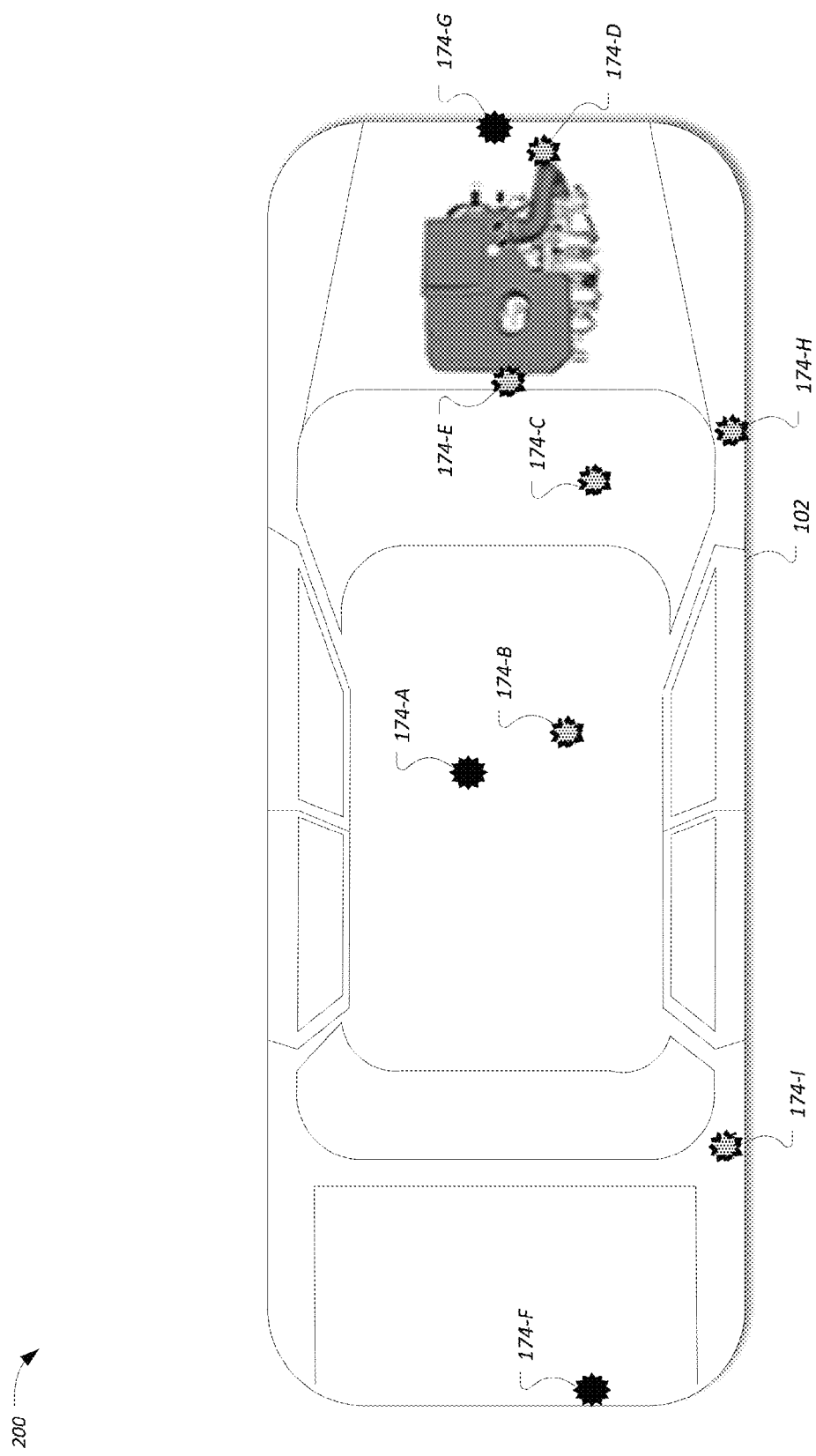
FIG. 2 illustrates an example of a vehicle including particulate sensors in various vehicle locations.

FIG. 2 illustrates an example 200 of a vehicle 102 including particulate sensors 174 in various vehicle 102 locations. For example, the vehicle 102 may include a particulate sensor 174-A on the roof of the vehicle 102 configured to monitor ambient air quality above the vehicle 102. As another example, the vehicle 102 may include a particulate sensor 174-B mounted to the underside of the vehicle 102 configured to monitor ambient air quality below the vehicle 102. The vehicle 102 may also include a particulate sensor 174-C located within the vehicle 102 cabin and configured to monitor cabin air quality.

The vehicle 102 may also include particulate sensors 174 configured to monitor the engine. In an example, the vehicle 102 may include a particulate sensor 174-D in an engine air intake configured to monitor the quality of air entering the engine, and/or monitoring the quality of air in the manifold after engine shutdown. In another example, the vehicle 102 may include a particulate sensor 174-E in the exhaust system configured to monitor engine airflow exiting the engine, and a particulate sensor 174-F in the exhaust system after the muffler configured to monitor engine airflow exiting the vehicle 102.

The vehicle 102 may also include particulate sensors 174 configured to monitor other vehicle 102 aspects. In an example, the vehicle 102 may include a particulate sensor 174-G mounted at the front bumper or other front vehicle 102 location and configured to monitor particulates encountered by the vehicle 102 as it drives, such as fog or black ice. In another example, the vehicle 102 may include a particulate sensor 174-H mounted in a wheel well and configured to monitor brake dust or tire dust or other particulate indicative of tire wear, brake wear, or potentially aggressive driving techniques. In yet a further example, the vehicle 102 may include a particulate sensor 174-I mounted near a fuel tank inlet and configured to monitor for vapors from the vehicle 102 fuel tank.

Using the particulate application 176, particulate sensors 174, particulate data 178, and remote telematics server 162, various in-vehicle 102 applications and vehicle 102 functionalities may be achieved.

In an example, the particulate sensors 174 may be utilized to increase the life of a vehicle 102 cabin air filter. For the comfort and health of the occupants of a vehicle 102 it is generally desirable to reduce the amount of particulates in cabin air while driving. Accordingly, some vehicles 102 are equipped with a cabin air filter to reduce the amount of particulate in the ambient air that is drawn into the vehicle 102. A new paper filter generally only removes particles greater than a size of the filter structure (e.g., 6 μm in an example), but becomes more effective at removing smaller particles as it becomes dirtier as larger particles get stuck in the filter. Eventually the filter becomes clogged and only passes the smallest particles, but also has insufficient air flow to be effective. A preferred time to change the filter is when the filter becomes clogged. Changing it too soon means additional cost for filters, but also means that over the life of the vehicle 102 the filter is more often "new" and therefore less effective.

The particulate application 176 may be configured to monitor the concentration of particles below a pre-determined threshold using the particulate sensor 174-C. When the concentration falls below the pre-determined threshold, the particulate application 176 may be configured to perform one or more actions. In an example, the particulate application 176 may raise an alert to instruct the driver to purchase and install a new filter. Since the vehicle 102 may also be connected to the cloud, the particulate application 176 may be further configured to contact a web service (e.g., Ford Parts) and purchase a cabin air filter to be delivered to an address associated with the vehicle (e.g., VIN number; MDN; telephone number; secure element ID "SEID"; device, etc.) 102 (e.g., based on a telematics account of the user). As a further possibility, the particulate application 176 may send a message that the filter needs replacement to an advertisement web service that delivers a promotional coupon to vehicle 102 occupants for a discount on a cabin air filter at a particular retailer or retail location to lure the customer into the store.

In some instances where the particulate application 176 utilizes the pre-determined threshold approach to filter lifespan, there may be situations where there are few particulates in the ambient air. In such a situation, the particulate application 176 may identify a lack of particulates and incorrectly infer that the cabin air filter needs to be replaced, when actually there are no particulates to be filtered. Accordingly, in some examples a second particulate sensor 174-C may be utilized at the filter inlet and connected to the vehicle 102 so that the particulate application 176 may be able to determine the difference in particulates entering and exiting the cabin filter. In this case, a pre-determined threshold ratio of particles input to and output from the filter within the correct size band (e.g., <4 μm) may be utilized. As the filter ages, the ratio may grow smaller, and when the ratio goes below the pre-determined threshold level the particulate application 176 may be configured generates an alert or purchase/purchase request, e.g., as discussed above.

In another example, the particulate sensors 174 may be utilized to control windows of the vehicle 102. Particulates may be created inside the vehicle 102. For example, an average person sloughs off about an ounce of epidermal cells daily. Or, a single cough produces 3000 particles of saliva frequently containing pathogens. A sneeze may be worse, potentially creating 40,000 particles at over 200 miles per hour. Some people smoke in vehicles 102, which also produces particulates in the form of smoke. The vehicle 102 interior also itself sloughs off particles, including plastic polymers from which aspects of the vehicle 102 are constructed. These particulates may settle through sedimentation in the cabin when the vehicle 102 isn't moving, but may be re-dispersed when a vehicle 102 door is opened. So, when a driver reenters the vehicle 102, the driver may be the recipient of a dose of vehicle 102 particulates. Moreover, many such particles may be circulated in the vehicle 102 by the vehicle 102 climate system.

Particulate sensors 174 (e.g., particulate sensors 174-A, 174-B and 174-C) may be installed inside the vehicle 102 cabin and outside the vehicle 102 connected to the system 100. When particulate levels inside the vehicle 102 rise above those outside the vehicle 102, the particulate application 176 may be configured to automatically open a window or sunroof to push or pull in fresh air, thereby reducing the particulate level. The ambient air temperature may also be received by the particulate application 176 from the vehicle 102 climate control system, and when the temperature is below a pre-determined level, the particulate application 176 may be configured to turn on the vehicle 102 cabin air blower set to provide heated air instead of opening the window.

In another example, when the vehicle 102 is configured to access the remote telematics server 162, the particulate application 176 may be configured to determine the vehicle 102 location, and query the remote telematics server 162 (or, e.g., a global information system web service, a pollen web service, a weather web service, etc.) to determine when the vehicle 102 is entering an area of particulates, such as near a particulate plume of a particulate emitter such as an industrial facility, agricultural facility, or wild fire. The particulate application 176 may be configured to receive a particulate signature 180 for the particulate emitter, and when it detects the signature 180 in increasing concentration via the particulate sensors 174 (e.g., via the particulate sensor 174-C in the cabin) notify the user to close the windows (e.g., with occupant confirmation).

In yet another example, the particulate sensors 174 may be utilized to control cabin air blower speed. The climate control system blower, while necessary for circulation of the climate controlled air and thermal comfort of the occupants, also tends to pick up and keep in suspension particles in the cabin air. This is true particularly after an event in the vehicle cabin such as a cough, sneeze, or cigarette lighting up has produced particulates. Since the vehicle blower pushes air filtered by the cabin air filter out of the vehicle 102, having the blower on high may reduce particulates in the cabin air by dilution. On the other hand, the blower may also only serve to stir up the particles and reduce the cabin air quality.

The particulate application 176 may be configured to utilize the particulate sensor 174-C to determine particulate level in the vehicle cabin, and identify a corrective action to take to reduce particulate level in the cabin. For example, when the particulate application 176 determines that there is a high concentration of particulates too small to be removed by the cabin air filter in the ambient air outside the vehicle 102, then the particulate application 176 may change the blower speed and adjust the climate control gates to reduce the inflow of ambient air. This determination may be made by using the outside the vehicle 102 (e.g., using the particulate sensor 174-A above the vehicle 102, using the particulate sensor 174-B below the vehicle 102, etc.) and/or by requesting particulate data 178 from the remote telematics server 162 for the current vehicle 102 location.

In another possible application, the particulate sensors 174 may be utilized to control a cabin air recirculation gate. Cabin air recirculation is intended to reduce the energy consumed by the climate control system by recirculating conditioned cabin air into the climate control system. However, recirculation may cause an accumulation of particulates and other materials in the cabin air. One such possibility is that the cabin air accumulates moisture from occupants breathing, hot food and drink, wet clothes, or other in-cabin sources of humidity. When the humidity of the cabin air increases, the dew point temperature also increases. When the dew point increases to the temperature of the glass in the vehicle windows, condensation may take place and may fog the windows. By receiving particulate data 178 from the particulate sense 174-C in the vehicle cabin, the particulate application 176 may be configured to identify when the cabin air exceeds a predetermined particulate threshold indicative of humidity, and may adjust the recirculation gate to permit outside air to enter to reduce the cabin humidity.

When a high level of particulates is anticipated outside the vehicle 102, the particulate application 176 may be configured to utilize the recirculation gate to prefer recirculated air. In an example, the particulate application 176 may be configured to request the remote telematics server 162 to provide particulate information for the current vehicle 102 location, and/or may receive particulate data 178 from a particulate sensor 174 outside the vehicle 102 (e.g., particulate sensor 174-A, particulate sensor 172-B, etc.), or by a fusion of the two. When the particulate data 178 indicates that particulate levels are higher outside the vehicle 102 then measured by the cabin particulate sensor 174-C, the particulate application 176 may be configured to adjust the recirculation gate to recirculate cabin air.

In yet another possible example, the particulate sensors 174 may be utilized for fog and black fog detection. When ambient temperature is near the dew point temperature and there are particulates from dust or fire that can nucleate condensation, black fog may be created near the ground surface. Some vehicle 102 system implementations derive the dew point and ambient temperature from ambient humidity and temperature sensors or from date, time, location, elevation, temperature and barometric pressure from the vehicle systems sensors. Some vehicle 102 systems also may derive the dew point and ambient temperature from a virtual humidity sensor that uses a cloud-based weather service which queries a remote telematics server 162 with a current vehicle location and returns the dew point and ambient temperature.

For instance, the particulate sensors 174-G may be utilized to determine particulate data 178 related to conditions at the front of the vehicle 102. Additionally or alternately, the particulate application 176 may utilize particulate data 178 for the current vehicle 102 location queried from the remote telematics server 162. (The particulate application 176 may also provide locally-determined particulate data 178 to the remote telematics server 162, as mentioned above.) The particulate application 176 may compare the received particulate data 178 to a particulate signature 180 indicative of humidity, dust particulates, or other conditions that may make fog creation likely. As some possibilities, conditions for fog creation may include, for example, existence of fires or salt particles form the ocean as nuclei for condensation when the humidity is high and the temperature is near the dew point. For example, the particulate signature 180 may indicate a signature for relevant particle types, as determined by the particle size distribution.

Using the particulate data 178, dew point and humidity, the particulate application 176 may be configured to detect conditions for fog and black fog. This estimate of the particulate signature 180 can be improved for connected vehicles 102 by prompting the vehicle 102 occupants if they observe fog. For instance, characteristics of particulate data 178 confirmed by the user as matching by the user feedback may be used to adjust the particle size and quantity information of the particulate signature 180 when the matching particulate data 178 consistently differs in some measurable respect from the particulate signature 180. Other sensors in the vehicle 102 may provide data to the particulate application 176 (e.g., via the vehicle bus 142 to the computing platform 104, from the computing platform 104 to the mobile device 152 via the device link interface 172, etc.). This data may include data from a rain sensor for the windshield, ambient light, time of day, day of year, location, map data with local topography and climate history, windshield wipers, fog light deployment, as some possibilities. Other sources of information may also be used, such as temperature history for the current vehicle 102 location, humidity history for the current vehicle 102 location, road surface temperature, visibility to known fiduciaries or other roadside units, brightness of headlights, and information from sounding equipment, vertical/horizontal wind speed etc. The particulate application 176 may query such information from web services or other sources of weather or climate data.

In another example, the particulate sensors 174 may be utilized for determination of tire and brake wear. When a brake pedal is applied by a driver, the vehicle 102 braking system may apply brake pads with brake rotors to produce friction, which causes reverse torque and also wears the brake rotors. Brake wear resulting from a braking event may be a factor of temperature, brake rotor surface conditions such as corrosion, materials on the rotors and pads, smoothness of the rotor which increases with time from the rotor surface being conditioned and the friction material, surface quality, friction surface area, and processing used to make the pads.

The particulate sensors 174-H may be utilized to receive particulate data 178 regarding brake wear. Based on the particulate data 178, the particulate application 176 may utilize particulate signatures 180 indicative of various brake conditions to estimate brake wear. This brake wear estimation may accordingly be used, in an example, to inform the driver of remaining pad life and end of pad life before the pad sound occurs.

With respect to tire wear, tire wear may occur when reverse torque from the brake is applied and/or tire cornering force caused the tire to lose traction and slip relative to the road surface. Or, poor front end alignment and loose or worn suspension components may contribute to tire wear. The particulate sensors 174-H may also be utilized to receive particulate data 178 regarding tire wear. Based on the particulate data 178, the particulate application 176 may utilize particulate signatures 180 indicative of tire particles conditions to identify tire wear conditions. This tire wear estimation may accordingly be used, in an example, to inform the driver that wear is high and the operator may learn to avoid those conditions.

Additionally, the particulate application 176 may be configured to utilize other sensors of the vehicle 102 to confirm tire or brake wear conditions. As some possibilities, the particulate application 176 may receive information including factors such as steering angle, wheel speed, anti-lock brake activation, ambient temperature, vehicle accelerations, brake activation, brake torque, brake pressure, traction control activation, as some possibilities.

As another possibility, the particulate application 176 may be configured to provide the particulate data 178 to the remote telematics server 162. Using the particulate data 178, the remote telematics server 162 may be configured to create roadmaps geocoded with tire wear data. The data may further be used, in an example, to provide for routing of vehicles 102 to avoid areas of high tire or brake wear. For instance, the remote telematics server 162 may associate road segments with tire wear scores based on vehicles 102 indicating tire wear in particulate data 178 uploaded to the remote telematics server 162. When vehicles 102 request routing information from the remote telematics server 162, the remote telematics server 162 may accordingly be able to take the wear scores into account when determining a low-cost route. It should be noted that the wear scores are merely an example, and the remote telematics server 162 may utilize the particulate data 178 to create routes avoiding particulate generally, or avoiding particulate matching other particulate signatures 180 (e.g., pollen, humidity, ash, etc.), as some other possibilities.

Figure 3:
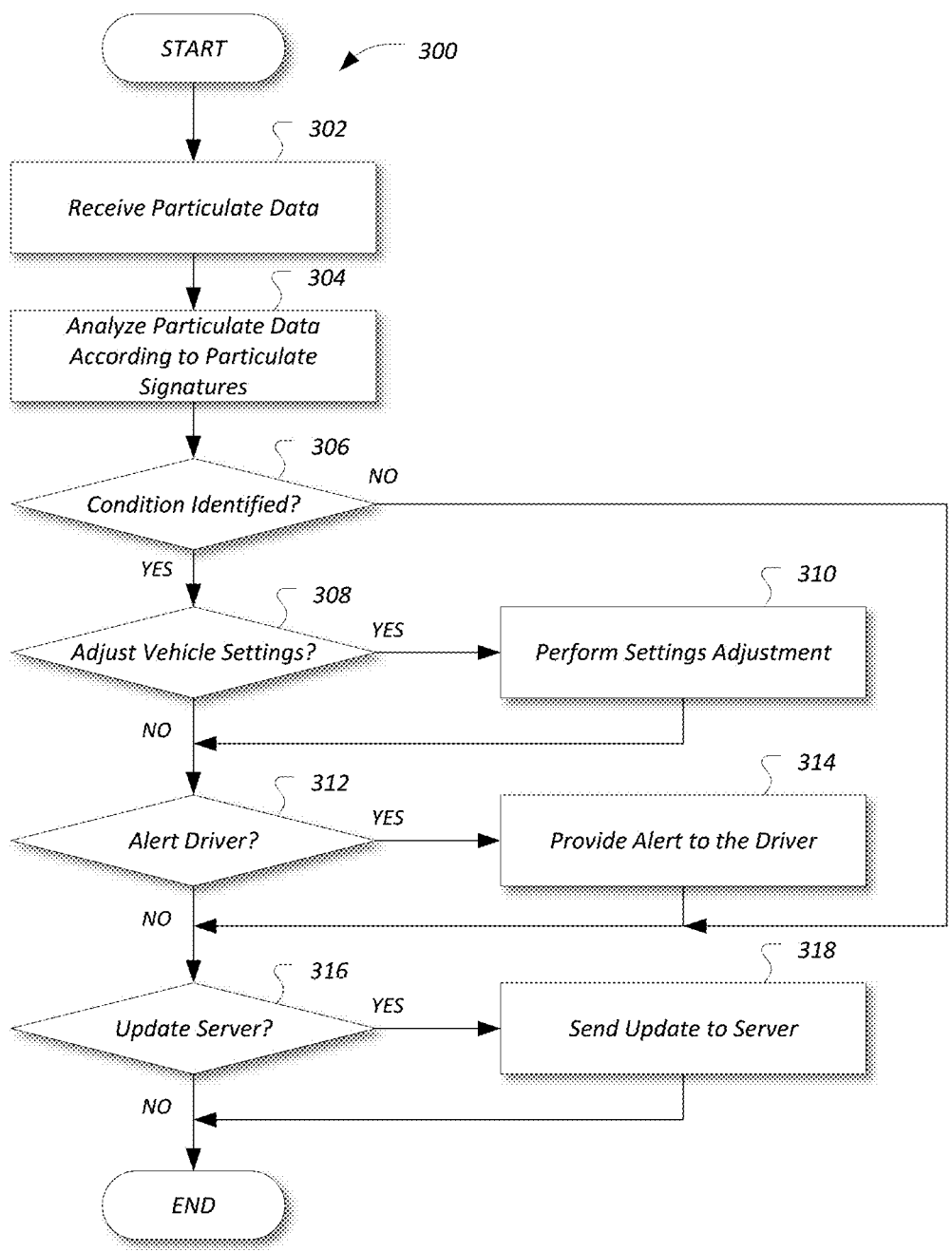
FIG. 3 illustrates an example process for utilizing particulate data from particulate sensors of a vehicle.

FIG. 3 illustrates an example process 300 for utilizing particulate data 178 from particulate sensors 174 of a vehicle 102. In an example, the process 300 may be performed by the particulate application 176.

At operation 302, the computing platform 104 receives particulate data 178. In an example, the particulate application 176 may receive the particulate data 178 from the particulate sensors 174 of the vehicle 102 via the vehicle bus 142. Some examples of particulate sensors 174 are described above with respect to FIG. 3.

At operation 304, the computing platform 104 analyzes the particulate data 178 according to one or more particulate signatures 180. In an example, the particulate application 176 may compare the particulate data 178 to particulate signatures 180. The particulate signatures 180 may include, for example, distribution of particle sizes that may be used to identify a type of emission or lack of emission.

In some examples, the computing platform 104 may analyze particulate data 178 from multiple particulate sensors 174 to identify differences between the particulate data 178 received from the different particulate sensors 174. For instance, the particulate application 176 may compare particulate data 178 measured within the vehicle cabin to particulate data 178 measured outside the vehicle 102 cabin. As another possibility, the particulate application 176 may compare particulate data 178 measured to air before entering a cabin air filter to particulate data 178 measured to air after exiting the cabin air filter. As yet another possibility, the particulate application 176 may compare particulate data 178 queried from the remote telematics server 162 for the current vehicle 102 location to particulate signatures 180.

As another variation, the computing platform 104 may receive particulate signatures 180 of current particulate conditions queried from the remote telematics server 162 from particulate data 178 provided from the vehicle 102 and/or other vehicles 102 for the current vehicle 102 location.

At operation 306, the computing platform 104 determines whether a particulate condition is identified. In an example, the particulate application 176 may determine that ash or other particulates are identified outside the vehicle 102, and that the vehicle 102 should have windows closed and/or switch to recirculating air. In another example, the particulate application 176 may determine that particulates within the vehicle 102 cabin are greater than those outside the cabin, and that the vehicle 102 should have windows opened and/or switch to outside vented air. In yet a further example, the particulate application 176 may determine that a vehicle 102 cabin filter is not passing sufficient air, and that the operator should consider cabin filter replacement. Or, the particulate application 176 may determine that tire wear or brake wear is occurring at one or more vehicle 102 wheels, and that the operator should drive differently or consider equipment replacement. If a particulate condition is identified, control passes to operation 308. Otherwise, control passes to operation 314.

At operation 308, the computing platform 104 determines whether to adjust vehicle 102 settings. In an example, the particulate application 176 may identify from vehicle 102 settings that certain setting adjustments, such as whether to use recirculating air or outside air, may be done automatically. If the particulate application 176 determines to perform automatic adjustment, control passes to operation 310. Otherwise control passes to operation 312.

At operation 310, the computing platform 104 performs a settings adjustment to the vehicle 102. In an example, the computing platform 104 may automatically adjust whether a vehicle vent uses recirculating air or outside air to prefer a source of air having fewer particulates. In another example, the computing platform 104 may automatically roll down or up windows to prefer a source of air having fewer particulates.

At operation 312, the computing platform 104 determines whether to alert the driver. In an example, the particulate application 176 may identify from vehicle 102 settings that identification or some or all types of particulates or of some or all conditions resulting from identification of particulate should be reported to the driver. In another example, the particulate application 176 may optionally be configured via vehicle 102 settings to inform the user of automatic settings adjustments. If the particulate application 176 determines to perform automatic adjustment, control passes to operation 314. Otherwise control passes to operation 316.

At operation 314, the computing platform 104 alerts the driver. In an example, the particulate application 176 may provide an alert in the form of one or more of a voice prompt, chime, and user interface text in a display 138 of the vehicle 102. As some possibilities, the alert may inform the user to open or close windows, to change to recirculating air or to outside air, to replace the cabin air filter, to drive in a manner producing less brake or tire particulate, to route around an area of expected particulate emissions, etc.

At operation 316, the computing platform 104 determines whether to update the remote telematics server 162. In an example, the particulate application 176 may be configured to provide particulate data 178 identified by the vehicle 102 to the remote telematics server 162. In another example, the particulate application 176 may be configured to update the remote telematics server 162 only when the particulate data 178 matches a particulate signature 180. If the particulate application 176 determines to update the remote telematics server 162, control passes to operation 318. Otherwise the process 300 ends.

At operation 318, the computing platform 104 sends an update to the remote telematics server 162. In an example, the particulate application 176 may be configured to provide the particulate data 178 and a current location of the vehicle 102 (e.g., a GPS location received from the GPS module 146) to the remote telematics server 162. After operation 318 the process 300 ends.

Figure 4:
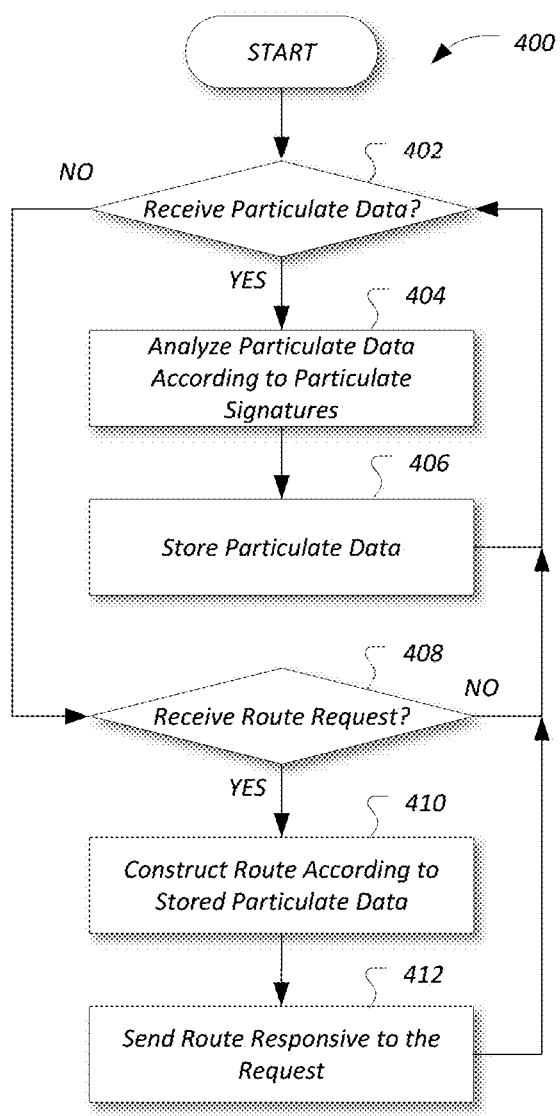
FIG. 4 illustrates an example process for utilizing particulate data by the remote telematics server for vehicle routing.

FIG. 4 illustrates an example process 400 for utilizing particulate data 178 by the remote telematics server 162 for vehicle 102 routing. In an example, the process 400 may be performed by the remote telematics server 162 in communication with a plurality of vehicles 102 over the communications network 156.

At operation 402, the remote telematics server 162 determines whether new particulate data 178 has been received. In an example, the remote telematics server 162 may receive particulate data 178 captured by particulate sensors 174 of the plurality of vehicles 102. In some cases, the vehicles 102 may be configured to report particulate data 178 periodically (e.g., every hour, every five minutes). Other reporting approaches are possible, such as reporting particulate data 178 every key on, every key off, every amount of distance traveled (e.g., every mile), or substantially in real-time when a connection from the vehicle 102 to the remote telematics server 162 is available. The received particulate data 178 may further include location and time metadata descriptive of where and when the particulate data 178 was captured. If particulate data 178 is received, control passed to operation 404. Otherwise control passes to operation 408.

At operation 404, the remote telematics server 162 analyzes the particulate data according to particulate signatures 180. In an example, the remote telematics server 162 may compare the particulate data 178 to particulate signatures 180. The particulate signatures 180 may include, for example, distribution of particle sizes that may be used to identify a type of emission or lack of emission.

At operation 406, the remote telematics server 162 stores the particulate data 178. In an example, the remote telematics server 162 may maintain the particulate data 178 indexed according to location and time.

At operation 408, the remote telematics server 162 determined whether a route request has been received. In an example, a vehicle 102 may request a route from one location from another, such as from a current vehicle 102 location to a point of interest location. The route request may further include information regarding options to use for generation of the route, such as types of particulate to be avoided. If a route request is received, control passes to operation 410. Otherwise, control passes to operation 402.

At operation 410, the remote telematics server 162 constructs a route according to the stored particulate data 178. In an example, the remote telematics server 162 may associate road segments with particulate level scores based on vehicles 102 indicating particulates in particulate data 178 uploaded to the remote telematics server 162. When vehicles 102 request routing information from the remote telematics server 162, the remote telematics server 162 may accordingly be able to take the particulate level scores into account when determining a low cost route. For instance, the route request may request a route avoiding road segments where excessive tire particulate is produced. Accordingly, the remote telematics server 162 may compare the particulate data 178 with particulate signatures 180 indicative of tire wear, and may associate road segments with the particulate data 178 matching the particulate signature 180 with a higher score than those without. The remote telematics server 162 may accordingly take the scores into account when determining a low cost route.

At operation 412, the remote telematics server 162 sends the route responsive to the request. The vehicle 102 may accordingly be informed of the requested route. After operation 412, control passes to operation 402.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A computer-implemented method comprising:
   receiving first particulate data from a first vehicle particulate sensor and second particulate data from a second vehicle particulate sensor;
   comparing the first and second particulate data to signature data identifying a particulate condition; and
   when only one of the first and second particulate data matches the signature data, one of (i) adjusting a vehicle setting to address the particulate condition and (ii) alerting a vehicle occupant of the particulate condition.

2. The method of claim 1, wherein the first particulate sensor samples an airflow before the airflow passes through a cabin air filter, the second particulate sensor samples the airflow after the airflow passes through a cabin air filter, and the particulate condition is particulates in the airflow below a predetermined threshold quantity.

3. The method of claim 1, wherein the first particulate sensor samples an airflow outside a vehicle, the second particulate sensor samples an airflow inside the vehicle, and the particulate condition is particulates in the airflows above a predetermined threshold quantity.

4. The method of claim 1, wherein the first particulate sensor samples a first airflow in a first vehicle wheel well, the second particulate sensor samples a second airflow in a second vehicle wheel well, and the particulate condition is particulates indicative of brake dust above a predetermined threshold amount.

5. The method of claim 1, wherein the first particulate sensor samples a first airflow in a first vehicle wheel well, the second particulate sensor samples a second airflow in a second vehicle wheel well, and the particulate condition is particulates indicative of tire dust above a predetermined threshold amount.

6. The method of claim 1, further comprising providing the particulate data and a location of the vehicle to a remote telematics server in communication with the vehicle over a communications network.

7. The method of claim 1, wherein the first particulate sensor includes a first micro-electromechanical systems sensor device having progressively finer filters for particulates for generating the first particulate data, and the second particulate sensor includes a second micro-electromechanical systems sensor device having progressively finer filters for particulates for generating the second particulate data.

8. The method of claim 1, wherein the signature data includes information indicative of size and quantity of ambient particulates associated with the particulate condition.

9. The method of claim 1, further comprising providing the first and second particulate data and a location of the vehicle to a remote telematics server in communication with the vehicle over a communications network.

\* \* \* \* \*